United States Patent [19]

Kaufman

[11] Patent Number: 4,977,904
[45] Date of Patent: Dec. 18, 1990

[54] ARTICLES FOR THE PROTECTION OF LIVING TISSUE

[76] Inventor: Jack W. Kaufman, 357 Frankel Blvd., Merrick, N.Y. 11556

[21] Appl. No.: 92,133

[22] Filed: Sep. 2, 1987

Related U.S. Application Data

[63] Continuation-in-part of Ser. No. 887,262, Jul. 21, 1986, abandoned, which is a continuation-in-part of Ser. No. 852,797, Apr. 16, 1986, abandoned, which is a continuation-in-part of Ser. No. 602,602, Apr. 20, 1984, Pat. No. 4,601,286.

[51] Int. Cl.$^5$ .............. A61B 19/08; A61B 19/12
[52] U.S. Cl. .................. 128/856; 128/850; 128/156
[58] Field of Search .......... 128/303.1, 207.14, 207.15, 128/155, 156, 82.1, 132 R, 132 D; 604/265, 266, 368

[56] References Cited

U.S. PATENT DOCUMENTS

| | | | |
|---|---|---|---|
| 3,862,452 | 1/1975 | Wichterle et al. | 128/334 R X |
| 3,901,236 | 8/1975 | Assarsson et al. | 604/368 |
| 3,975,350 | 8/1976 | Hudgin et al. | 128/127 X |
| 4,053,442 | 10/1977 | Jungr et al. | 224/2.2 X |
| 4,058,124 | 11/1977 | Yen et al. | 604/376 X |
| 4,085,168 | 4/1978 | Milkovich et al. | 524/910 X |
| 4,173,606 | 11/1979 | Stoy et al. | 623/2 X |
| 4,362,841 | 12/1982 | Minatono et al. | 128/156 X |
| 4,390,656 | 6/1983 | Weise et al. | 524/493 |
| 4,411,885 | 10/1983 | Barels et al. | 424/49 X |
| 4,452,776 | 6/1984 | Refojo | 264/2.5 X |
| 4,468,229 | 8/1984 | Su | 8/543 X |
| 4,489,722 | 12/1984 | Ferraro et al. | 128/207.15 |
| 4,524,064 | 6/1985 | Nambu | 514/944 X |
| 4,548,979 | 10/1985 | Weise et al. | 524/403 |
| 4,601,286 | 7/1986 | Kaufman | 128/132 D |
| 4,710,194 | 12/1987 | Kelman | 623/6 |

Primary Examiner—Robert A. Hafer
Assistant Examiner—Kevin G. Rooney
Attorney, Agent, or Firm—Seymour G. Bekelnitzky

[57] ABSTRACT

An article for the protection of humans, animals and other articles from damage due to undesired exposure to lasers comprising a tubular element comprising at least one layer comprising a xerogel comprising at least one water-insoluble hydrophilic polymer wherein if said tubular element comprises at least three layers the layer adjacent the distal side, relative to the laser beams, of said xerogel layer comprises a metallic layer the proximal surface of which may be reflective or nonreflective of the laser beams and wherein said xerogel layer may further comprise a pigment. In addition, the layer on the distal side of said metallic layer may be a xerogel. During use of the articles of the invention the xerogels thereof are in a hydrated condition, i.e., they are hydrogels.

21 Claims, 3 Drawing Sheets

ARTICLES FOR THE PROTECTION OF LIVING TISSUE

This application is a continuation-in-part of my copending application Ser. No. 877,262 filed Jul. 21, 1986, now abandoned, which was a continuation-in-part of my copending application Ser. No. 852,797 filed Apr. 16, 1986, now abandoned, which was a continuation-in-part of my copending application Ser. No. 602,602 filed Apr. 20, 1984 now U.S. Pat. No. 4,601,286 issued Jul. 22, 1986.

BACKGROUND OF THE INVENTION

This invention relates to articles for the prevention of undesired exposure of humans, animals and articles to laser beams. More particularly, it relates to protective barriers such as protective clothing, sheaths for instruments, surgical drapes, endotracheal tubes, vaginal dilators and the like, for use in or during laser-effected surgery or therapy which are useful in the protection of such humans, animals and articles from said undesired exposure to said lasers, said barriers being comprised of hydrophilic xerogels or hydrogels and, if desired, additional additives such as salts, colorants, pigments and medications.

Lasers have recently made a significant breakthrough as a preferred, in some, and the only modality, in other surgical and therapeutic areas. These areas of increasing use of lasers in surgery and other treatments include, e.g., otolaryngology, gynecology and ophthalmology.

Amongst the main advantages of lasers, in surgery, are their ability to incise and/or remove precisely controlled areas of tissue while permitting visual assessment of the procedure through use of an operating microscope. This visual assessment is facilitated by reduction of bleeding and absence of other instrumentation, which might block the surgeon's view, in laser surgery when compared to conventional surgical techniques.

Furthermore, if the blood vessels are sufficiently small they are sealed, by the laser, after incision. If some bleeding were to occur, for instance, in the case of larger blood vessels it can be efficiently stopped by coagulation using a defocused beam, the defocusing being accomplished by partial retraction of the focusing tip, i.e., by increasing the working distance of the laser beam.

Additional advantages of using lasers in surgery are the limitation of the area of undesirable tissue destruction and the zone of devitalized tissue, fewer post-operative complications and less post-operative pain and scar formation which might hinder healing. As a consequence hospitalization time is reduced.

Nevertheless, the use of lasers, in medical treatments and surgery, is not without disadvantages and hazards, chief among which are the danger of fire and the destruction of viable tissue on the margins, or periphery, of the operative site.

As a consequence normal drape procedures commonly used in lasser surgery and treatment are of limited value and potentially dangerous. For instance, a fire hazard is especially present when wet Cottonoids (cotton gauze pads wet with saline) which are used to protect the surrounding tissues and organs from exposure to extraneous laser beams, whether direct or reflected, dry out and ignite due to the high inflammability of dry cotton or cellulosics. This is an always present danger due to the high levels of energy associated with laser beams. Thus, it is necessary for the surgical team to be constantly aware of that possibility and to keep the gauze moistened at all times.

Yet other problems arise in the use of drapes on compound surfaces, i.e. surfaces that are not smooth but rather have cavities and ridges, whereby the usual drapes do not conform to the surface topography thereby permitting gaps to be formed between the tissue surface and drape. These gaps permit the gathering of gases and/or heat therein which ultimately result in undesireable tissue damage.

Furthermore, stray beams may impinge on personnel and articles within the operating arena with concomitant damage thereto, e.g., burning the skin of said personnel, charring of clothing, melting of plastic articles, ignition of flammable materials, overheating of equipment, and the like. A. H. Andrews, Jr., and Polanyi, T. G., "Hazards and Safety Considerations When Using the $CO_2$ Laser" in A. H. Andrews, Jr. (ed.): *Microscopic and Endoscopic Surgery With the $CO_2$Laser*, Boston, MA., John Wright—PSG. Inc., pp 75–6, 1982.

An additional aspect of the fire hazard is that the laser beam will burn through most plastics or rubbers of which tubes for insertion into body cavities, e.g., endotracheal tubes and vaginal drapes or dilators, are constructed. Thus, the use of plastic or most rubber endotracheal tubes is usually contraindicated when surgery employing lasers is contemplated. Therefore red rubber tubing or steel, which are less sensitive to lasers, are used, e.g., in the construction of endotracheal tubes. However, because endotracheal tubes prepared from such materials lack built-in cuffs, they do not make completely air-tight seals with the organ walls. To get around that problem it has been necessary to place a separable, inflatable cuff over the distal end of the tube which has, therefore, resulted in the addition of a balloon-filling tube, passed through the larynx, to an already crowded lumen. Furthermore, if the beam impacts upon such a cuff it usually creates a hole or holes therein whereby the inflating medium escapes with a resultant deflation of the cuff and undesirable and potentially dangerous mixing of the environments normally separated by the cuff.

A method to prevent such an occurrence by disposing a thermal shield, comprising a plurality of laser-reflecting petals extending from the outer walls of said tubes to the inner walls of the cavity, between the cuff and the portion of the cavity wherein the surgery or treatment is to be performed, is taught in U.S. Pat. No. 4,378,796.

However, as the above shield functions by "reflecting" the laser beam its use would be diadvantageous to the patient in that the reflected beam may then impact upon healthy tissue, rather than on the surgical site, with deleterious effects thereto.

Additional protection against such undesired impact by the "laser beam [may be provided] by wrapping the tube with an aluminum adhesive tape". . . However, [a]lthough the aluminum tape provides protection, it should not be relied on heavily. . . The tape is only a safety factor and is not absolute." Ibid, p. 77.

Another problem, the destruction of viable tissue near the operative site is due to the fact that, during surgery using lasers, it is often impossible to concentrate the laser exactly and exclusively on the surgical site. For instance, the incident beam may have a larger diameter than the surgical site or part of the beam may be dispersed or reflected, although at a lower intensity, to a distance from the surgical site. This results in undesireable destruction of healthy tissue at the periphery of, and/or at a distance from, the surgical site. The damage occurs in the same manner as the surgery is effected, i.e., by ablative removal of the water (about 90%) and organic matter of which the tissue is comprised.

It has now been found that the articles of the instant invention obviate the above problems thereby providing for enhanced protection of humans, animals and articles during laser-effected surgery and treatments whereby healing of the wounds is facilitated.

SUMMARY OF THE INVENTION

Accordingly, it is an object of this invention to provide articles for the protection of humans, animals and other articles from damage due to undesireable exposure to stray or reflected laser beams used during laser-effected surgery.

It is yet another object of the invention to provide an article for the protection of humans, animal and articles from damage due to exposure to laser beams during treatment or surgery using lasers said article comprising a hydrophilic xerogel.

Yet another object of the invention to provide a laser-resistant tube, to be utilized by passage of laser beams therethrough or externally thereof, for insertion into body cavities, whereby unwanted exposure to said beams, directly or indirectly, is prevented.

According to another object of the invention there is provided a tube as described above comprising at least two layers at least the one proximal to the laser beams comprising a xerogel.

In accordance with yet another object of the invention there is provided a tube as described above wherein the layer on the distal side of said metallic layer also comprises a xerogel.

According to still another object of the invention there is provided a tube as described above comprising a tube which is encircled near its distal end by an expandable cuff, said tube and cuff comprising at least one hydrophilic xerogel and water.

Yet another object of the invention is to provide a tubular article comprising at least one layer comprising a hydrophilic xerogel as described above said tube further comprising at least one metallic layer adjacent the xerogel layer proximal the incident laser beam.

Another object of the invention is to provide an article as described above wherein the surface of said metallic layer adjacent said xerogel layer is non-reflective of said laser beams.

Yet another object of the invention is to provide an article as described above wherein said xerogel layer further comprises pigments to absorb the unwanted radiation.

Another object of the invention provides a protective artiocle as described above wherein the xerogel layer thereof further comprises pigments to absorb, and the metallic layer comprises a surface non-reflective of said, undesired radiation.

These and other objects of the invention will be in part discussed and in part apparent upon consideration of the detailed description of the preferred embodiment.

BRIEF DESCRIPTION OF THE DRAWINGS

FIG. 13 is an elevational perspective view of a modification of the embodiment of FIG. 4.

FIG. 14 is a front elevational view of the embodiment of FIG. 13.

FIG. 15 is a plan view of the above embodiment along line 14—14 of FIG. 14.

DETAILED DESCRIPTION OF THE PREFERRED EMBODIMENT

Figure 1:
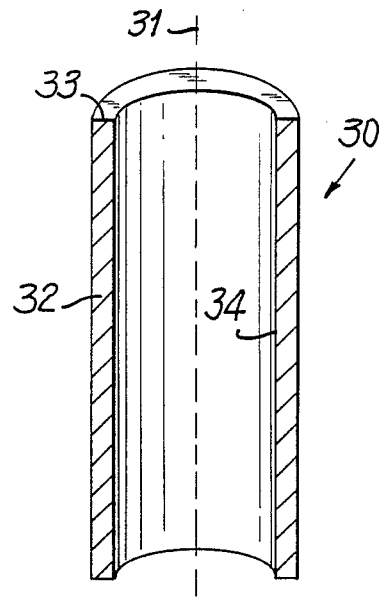
FIG. 1 is a front sectional view of the instant invention.

In accordance with the invention it has now been found that humans, animals and articles may be protected from damage due to undesired exposure to laser beams by disposing protective barriers, comprising at least one xerogel, between said laser beams and the item to be protected said xerogel comprising at least one hydrophilic water-insoluble polymer.

Thus, in accordance with this invention there is provided an article for the protection of humans, animals and articles from damage due to undesired exposure to laser beams comprising A. A hydrophilic xerogel comprising at least one water-insoluble hydrophilic polymer;

B. Water;

and C. If desired, at least one additive such as a medication, colorant, pigment or moisturizer.

The hydrophilic polymers useful in accordance with the invention are those which are inherently water-insoluble and those which may be rendered so by cross-linking.

Examples of inherently water-insoluble hydrophilic polymers include copolymers of hydrophobic monomers, such as acrylonitrile, acrylates, (e.g., methyl and ethyl) methacrylates, (such as methyl and propyl) and styrene with hydrophilic monomers such as, acrylamide and acrylic and methacrylic acids. Other inherently water-insoluble hydrophilic polymers may be exemplified by hydrophobic polymers such as silicone, acrylate, methacrylate and urethane polymers whose surfaces have been rendered hydrophilic by treatments such as partial hydrolysis of e.g., ester and amide groups and by grafting of hydrophilic monomers or other functional groups to the hydrophobic backbones.

The inherently water-insoluble hydrophilic polymers useful in the practice of the instant invention include the acrylonitrile-acrylamide copolymers described in U.S. Pat. No. 4,331,783 (issued 5/25/82) and the modified acrylonitrile-acrylamide copolymers described in U.S. Pat. No. 4,337,327 (issued 6/29/92), both patents being incorporated herein for reference.

Other polymers of this nature include block copolymers of poly(ethylene oxide) and relatively hydrophobic materials such as polyurethanes which are described, e.g., by E. W. Merrill and E. W. Salzman in their article "Poly(ethylene oxide) as a Biomaterial" (Am. Soc. for Artificial Internal Organs Journal, April/June 1983, pp. 60-64). Such materials are exemplified by Polyox TM, a crosslinked poly(ethylene oxide).

Water-soluble polymers which may be rendered insoluble by crosslinking include polymers of hydrophilic monomers such as those mentioned above, hydroxyalkyl acrylates and methacrylates and alkylene oxides such as those of ethylene and propylene. Such crosslinked hydrogels are described in, e.g., U.S. Pat. No. 3,320,960 (issued 11/30/65) and U.S. Reissue Pat. No. Re27,401 (6/20/72).

Preferred insoluble hydrophilic polymers useful in the practice of the invention are the acrylonitrile-acrylamide and poly(ethylene oxide) copolymers described above.

The particular choice of water-insoluble hydrophilic polymers for use in the articles according to the invention will depend on the specific purpose to which the article is to be applied. For instance, if the article is to be used extracorporeally, e.g., as an article of clothing, the polymer type is unlimited, whereas if the article is to be used in contact with the body, e.g., in an endotracheal tube the type of polymer will depend on, for instance, the $pK_a$ thereof and any other factors which could affect biocompatability with the specific body part in contact with the protective article.

Crosslinking may be effected by addition of crosslinking compositions, such as those which decompose into free radicals and polyfunctional materials; by exposure to radiation and by other means known to those skilled in the art.

Examples of compositions which decompose to form free radicals are azonitriles, such as azobis(isobutyronitrile): peroxides, such as benzoyl peroxide; and hydroperoxides, such as cumene hydroperoxide.

Polyfunctional materials useful in crosslinking hydrophilic polymers include the acrylates and methacrylates of polyhydric compounds such as diols, e.g., ethylene glycol; triols, such as glycerol and 1,1,1-tris(hydroxymethyl)propane; tetraols, e.g., pentaerythritol and polyhydric polymers such as epoxy resins. Other crosslinking agents which may be used in the practice of the invention, as well known in the art, include zinc oxide, organotin compounds, N,N'methylenebisacrylamide and diallylidene pentaerythritol.

Radiation-induced crosslinking may be effected by actinic radiation such as UV and visible light; $\gamma$-radiation; and electron beams.

As the sources of laser light provide light of varying wavelengths (e.g., the $CO_2$ laser at 10.6$\mu$, the Argon laser at 0.48$\mu$ [i.e., in the blue region of the spectrum] and the ruby laser in the red region at 0.69$\mu$) it is often necessary to add colorants to the hydrogel to prevent transmission of the laser beams therethrough. Added colorants are not needed only in the case of the $CO_2$ laser, whose light is strongly absorbed by water and, therefore, all tissues.

If the article is to be used in contact with the body the particular crosslinking method must be such as will yield a product which will not depolymerize or decompose, to yield products which are water-soluble, when exposed to the body environment in which they are used or the operating media.

The protective article may be of any shape or form known in the art such as, sheets, sheaths, tape, dressings, fiber optic tubes, surgical drapes, including laser-transmitting tubes, such as vaginal dilators and retractors, and the like, and endotracheal tubes. The particular form to be used at any one time would depend upon the requirements of the user. The protective articles may be adhesive or non-adhesive to the surface to be protected and the adhesion may be effected through autoadhesion or adhesives.

In accordance with this invention there is provided a laser barrier comprising a hollow tubular element comprising two layers with the provisos that (1) if the laser is to be used by passing it through the lumen of said element at least the innermost layer comprises said xerogel;

and (2) if said laser is to be used opposite the outer wall of said element at least the outermost layer comprises said xerogel.

Another aspect of the above embodiment provides for an at least three layered structure wherein at least one of said layers is metal composition disposed between (1) said innermost xerogel layer and the first non-xerogel outer layer when the laser is to be used by passing it through the lumen of said element;

or (2) said outermost xerogel layer and the first non-xerogel inner layer when the laser is to be used opposite the outer wall of said element.

According to a modification of the above aspect the layer on the distal side of the metallic layer also comprises a xerogel.

It has been found that if the lasers are improperly used, e.g., by an excessive period of exposure, they may burn through the hydrogel layer. The damage resulting therefrom may be reduced or eliminated by further modification of the above embodiments.

Thus, in another modification of the invention the proximal surface of the metallic layer is made non-reflective to the laser beams. The methods for preparing such surfaces is known to the art and will not be described further.

It has also found that the consequences of such improper use may be abated, especially in the absence of such metallic layers, by dispersing pigments throughout the xerogel layer.

Pigments useful in the practice of this aspect of the invention include inorganic and organic pigments wherein the inorganic pigments are selected from the group comprising $TiO_2$, $ZnO$, the basic white carbonates, sulfates, and silicates of lead, $ZnO$, lithopone, $Sb_2O_3$, $CaCO_3$, silicates of Mg and Al, pyrophillite, bentonite, mica, pumice, $BaSO_4$, $CaSO_4$, MgO, $SiO_2$, diatomite, and powders of Al, Cu, Zn, Pb, Au, Ag, Ni and their alloys, bronzes and Stainless Steel.

Preferred pigments for use in this aspect of the invention may be selected from the group comprising $TiO_2$, ZnO, $Sb_2O_3$, silicates of Mg and Al, pyrophillite, bentonite, mica and pumice and powdered Al.

A most preferred pigment for use in the practice of this aspect of the invention is $TiO_2$.

As required for specific uses the articles according to this embodiment of the invention will also comprise means for inserting, removing and manipulating same, e.g., handles in the case of vaginal dilators, means for hydrating the xerogels, to form hydrogels, e.g., such as those described for passing inflating gases to the inflatable balloons described in, for example, U.S. Pat. Nos. 4,378,796 and 4,489,722.

In accordance with another embodiment of the invention there is provided an article comprising a tube for use in laser surgery or treatment, comprising at least one layer comprising a a xerogel comprising any of the afore-mentioned water-insoluble hydrophilic, polymers which is on its inner surface plated to a mirror finish which will reflect any extraneous laser beams incident thereon. (Of course, in the case where the polymers are not initially water-insoluble crosslinking must occur concurrently with, or after, formation of said tube.) Any beams which pass through said inner surface are absorbed in the tube walls and the energy thereof dissipated.

Another aspect of the above embodiment provides for such a tube which is filled with a silver halide material as transmitter of the laser beam. The silver halides useful in the practice of the invention are well known in the art and will not be discussed further.

The metallic layer may be applied to one of said inner layers while in adhesive or non-adhesive contact therewith and with the layer on its opposite surface, in the form of a sheet or tape wound around said xerogel layer. It may also be used in the form of concentric tubes, including segmented tubes such as "BX" cable, which may be in contact with one or both layers adjacent thereto or spaced therefrom. If desired, the metal may also be applied to the inner layer in the form of a powder dispersed through a binder matrix by any of the means known to one skilled in the art.

Other methods of using the protective articles will be determined by one skilled in the art in accordance with the specific application.

The metals useful in the practice of this embodiment are selected from the group comprising aluminum, gold, titanium, silver, their alloys, and the like. Preferred metals for use in accordance with the invention are aluminum and gold and their alloys. The most preferred metal for use in accordance with the invention is aluminum.

It is believed, although the theory is not essential to the practice of the invention, that the article protects the covered portions of the tissue by absorption of the energy of the laser beam incident thereon in the contained water which dissipates the absorbed energy by evaporation. A portion of the energy is also believed dissipated by scission of the organic portion of the article and ablation thereof.

In yet another embodiment of the invention there is provided a method of applying laser light to a desired tissue site, without undesirable damage due to stray or reflected laser beams, for treatment or surgery, by transmission of said light through a tubular instrument (e.g., a fiber optic) which focuses said light on the operative site and does not permit escape of extraneous reflected or dispersed light to the atmosphere or by transmission of gases, such as anesthetics and/or oxygen, or passage of instruments through the tube while the treatment or surgery is performed opposite the outer wall of the tube, said tubular instrument, comprising at least one layer comprising A. A hydrogel comprising
1. At least one hydrophilic xerogel;
and 2. Water and B. If desired, at least one additive such as a medication, colorant or moisturizer.

The hydrogels and additives useful in the practice of this embodiment of the invention may be selected from those described above.

In another modification of the above embodiment the tube comprises a multilayered structure wherein (a) if the article is to transmit the laser at least the innermost layer comprises said hydrogel;

and (b) if the article is to transmit gases at least the outermost layer comprises said hydrogel.

The multilayered structure may be formed by coextrusion of the layers or the layers may be caused to bond to each other adhesively by means of separate adhesives or self-adhesively.

In the case of gas transmitting tubes, such as endotracheal tubes, the outer hydrogel layer may be placed upon the inner tube as a lengthwise incised sheath or slipped over the inner layers as a seamless tube. Adherence of the tubes to each other may be adhesive, as in the above indicated embodiment, or non-adhesive.

If the laser beams are to be applied through the tube the inner xerogel layer may be inserted into the hollow formed by the outer layers and retained therein either by force fitting or adhesively.

Furthermore, in accordance with another aspect of this embodiment of the invention the tubular element is plated on its inner surface to a mirror finish which will reflect most of the extraneous laser beams incident thereof and absorb the energy of any beams not reflected.

If desired, the above tube may be filled with a silver halide as a transmitting medium. Silver halides for use in accordance with the invention are well known in the art and will not be discussed further.

In the gas transmitting mode when the tube comprises more than one layer at least the outermost layer comprises said hydrogel.

In another modification of this embodiment a metallic layer is disposed (a) in the gas transmitting mode between said outermost layer and the gas transmitting path;

and (b) in the light transmitting mode between said innermost layer and said organ wall.

In a multilayered structure the metallic layer may be any of the layers other than (a) the outermost in the gas transmitting mode;

or (b) the innermost in the light transmitting mode.

The metals useful in this embodiment may be any of those described above or known in the art and their method of application may be any of those known in the art.

Throughout the application the metal surface in the path of the stray beams may, as desired, be reflective or non-reflective of the laser beams.

Referring now to FIG. 1, there is shown an embodiment 30, of the invention, comprising a hydrophilic xerogel tube 32. The laser beam 32 passes through said tube to the site to be lased.

In modifications of the above embodiment the inner wall 34 of said tube may be plated to reflect stray beams and/or the tube may be filled with laser-transmitting materials, such as silver halides, and sealed at both ends with laser-transmitting end caps and/or handles for manipulating said tubes may be attached to the proximal edges 33 thereof.

Figure 2:
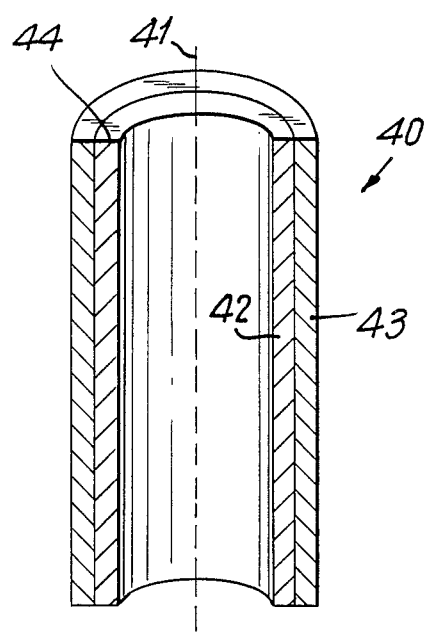
FIG. 2 is a sectional view of an alternate embodiment of the tube of FIG. 1.

FIG. 2 shows an alternate embodiment 40 of the laser-transmitting tube of FIG. 1 comprising two concentric tubes 42 and 43 wherein the inner tube 42 comprises a hydrophilic xerogel. The outer tube 43 comprises any material known, in the art, for such purposes, such as metals and rigid or semi-rigid plastics or rubbers. Said tube may also comprise a hydrophilic xerogel. The xerogels of tubes 42 and 43 may be the same or different. The tubes may be joined, at their interface, adhesively or non-adhesively.

Said tubes may be coextruded or the hydrophilic tube 42 may be inserted into tube 43 after formation thereof.

In another embodiment (not shown) when the laser is to be used externally of the tubular element the tube 43 would have to comprise said xerogel.

In yet another alternate embodiment, not shown, of the tube of FIG. 2 a third hydrophilic xerogel tube may be placed on the outside of tube 43. Said tube may be applied as indicated above or as a sheath cut lengthwise for application, or a seamless tube to be slipped over, the inner layers of the tubular element 40.

Figure 3:
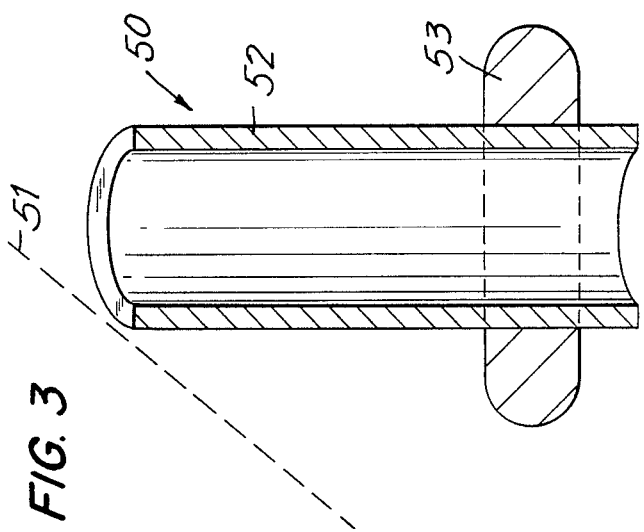
FIG. 3 is a sectional view of another embodiment of the tube of the instant invention.

FIG. 3 illustrates another aspect of the invention comprising a laser-resistant tube 50 comprising a hydrophilic xerogel tube 52 and an expandable hydrophilic xerogel cuff 53 encircling and adhesively joined to said tube 52 near its distal end. The laser beam 51 is directed to the desired site opposite the outer wall of tube 50.

Figure 4:
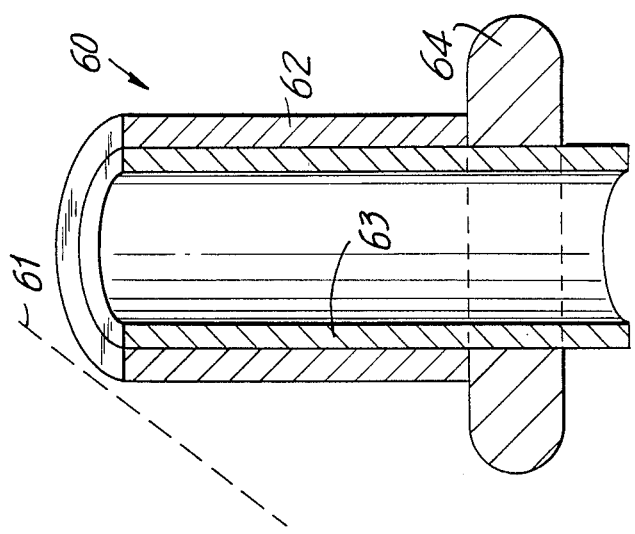
FIG. 4 is a sectional view of another embodiment of the tube of FIG. 3.

In FIG. 4 there is illustrated an alternate embodiment 60 of the tube of FIG. 3 comprising two concentric tubes 62 and 63. Tube 62 comprises a hydrophilic xerogel and tube 63 materials selected from the group comprising metals, flexible rubbers and plastics and hydrophilic xerogels. The hydrophilic xerogels of tubes 62 and 63 may be the same or different. Tube 62 terminates at the expandable cuff 64 which encircles tube 63.

Figure 5:
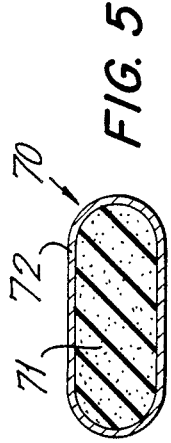
FIG. 5 is a sectional view of one embodiment of the expandable cuff of FIGS. 3 and 4.

FIG. 5 illustrates an expandable cuff 70 for any of the above tubular elements comprising an expandable sponge 71. If the sponge 71 comprises a hydrophobic porous material it is enclosed within a water-impermeable covering 72. If, however, sponge 71 comprises a hydrophilic xerogel said covering is not necessary.

Figure 6:
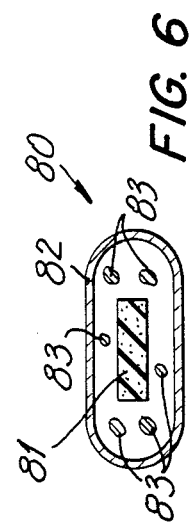
FIG. 6 is a sectional view of another embodiment of the expandable cuff of FIGS. 3 and 4.

In FIG. 6 there is shown an alternate embodiment 80 of the cuff of FIG. 5 comprising a water-expandable sponge 81 and a water-impermeable covering 82. In order to decrease the possibility of formation of holes, resulting in leakage of the inflating medium and deflation of the cuff, due to inadvertent impact of the laser beams on the cuff there are disposed, between said sponge 81 and said covering 82 a plurality of particles 83 comprising at least one hydrophilic xerogel.

In another alternate embodiment, as illustrated in FIGS. 13-15, of the tubular element of FIG. 4 the tube 62 is terminated in a plurality of flaps 120, formed by a series of longitudinal incisions in the distal end of said tube, said flaps overlying and thereby protecting the cuff 64 from being impacted by stray laser beams. This is especially desirable when said cuff comprises a hydrophobic porous sponge and a water-impermeable covering.

In the practice of the invention the hydrophilic xerogels are hydrated, by either water or aqueous solutions of the aforementioned additives, prior to, or after, insertion of said tubes whereby the xerogels of the tubes and cuffs form hydrogels and the cuffs of the endotracheal tubes expand to close the passages into which the tube has been inserted.

Here again, as required, water or an aqueous solution of the additives may be applied to the protective article to replace any water lost during the treatment, e.g., by ablation due to the laser energy absorbed and/or evaporation to the environment.

Methods for preparing the articles of the invention are known to the art and will not be discussed further.

With respect to FIGS. 7 to 12 it is seen that the laser beams are transmitted, as in the use of a vaginal dilator, through the tubular element. It is to be understood that similar configurations are applicable where the laser beams are used externally to the tubular element, e.g., in the case of an endotracheal tube. In that instance the relative positions of the layers are the same as in the prior case and only their spatial positions are reversed.

Figure 7:
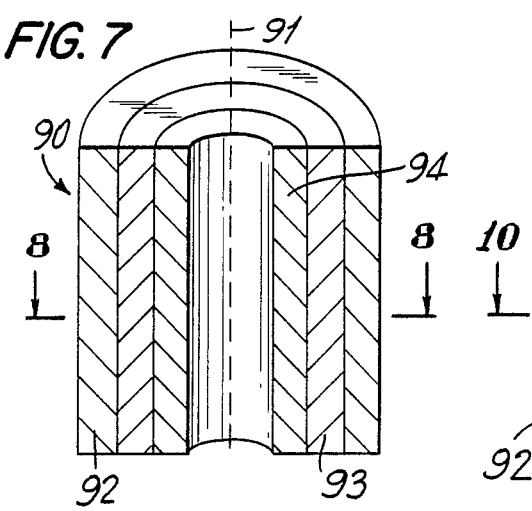
FIG. 7 is a front elevational sectional view of another embodiment of the tube of the invention.
Figure 8:
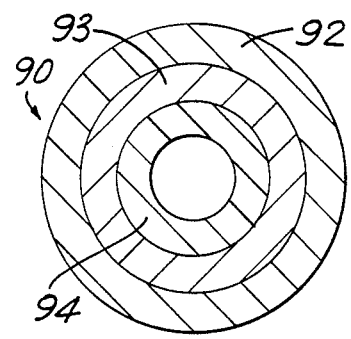
FIG. 8 is a sectional view taken along line 8—8 of FIG. 7.

FIGS. 7 and 8 illustrate a three layered tubular element 90 wherein at least the inner layer 94 comprises a xerogel as described above. The middle layer 93 may comprise a metal composition or any other composition indicated by the user's needs.

Figure 9:
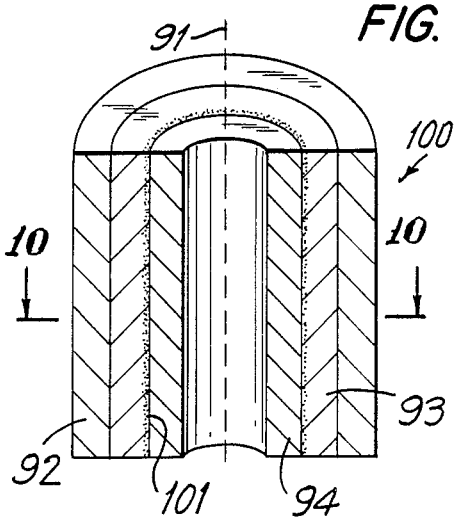
FIG. 9 is a sectional view of an alternate embodiment of the tube of FIG. 7.
Figure 10:
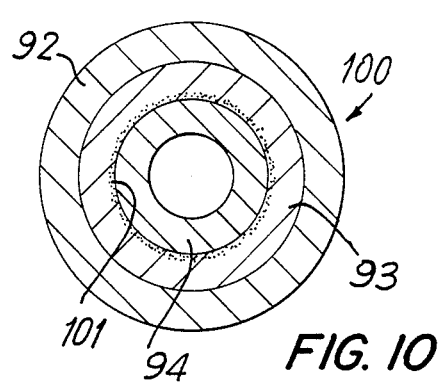
FIG. 10 is a sectional view taken along line 10—10 of FIG. 9.

FIGS. 9 and 10 show another aspect of the tubular element of FIGS. 7 and 8 wherein the middle layer 93 comprises a metal composition the proximal surface of which is non-reflective of the laser beams.

Figure 11:
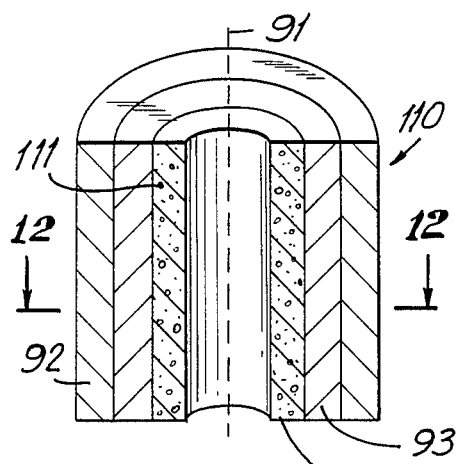
FIG. 11 is a sectional view of yet another embodiment of the tube of FIG. 7.
Figure 12:
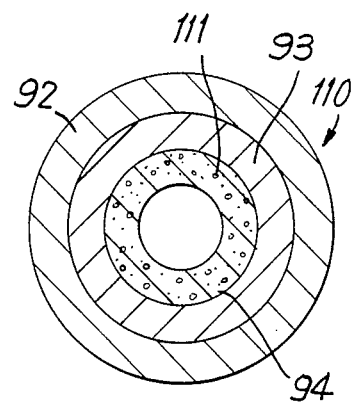
FIG. 12 is a sectional view taken along line 12—12 of FIG. 11.

In FIGS. 11 and 12 the inner, xerogel, layer further comprises at least one pigment dispersed therethrough.

In another aspect (not shown) the tubular element of FIGS. 7 and 8 may, if desired, comprise an inner tube 94 through which said pigment is dispersed and a middle layer 93, comprising a metal, whose proximal surface is non-reflective. The outer layer 92 will comprise any of the materials of construction known in the art.

In the practice of using the protective article of the invention the tubular element is inserted into the body cavity within which the laser surgery or therapy is to be effected. Prior to insertion the xerogel layer will be comprised of the additives if any.

The xerogel is converted to a hydrogel by hydration with water or an aqueous solution, e.g., of the additives, if any, prior to application of the laser. The hydration step may, as desired, precede or follow insertion of the article.

In most cases the hydration will precede insertion of the article to increase lubricity and, therefore, insertion thereof.

However, there may be instances, e.g., when the orifices are small, when it will be desireable to insert the dry tubular element into the cavity and then effect the hydration. The user will, of course, decide this on a case-by-case basis.

Changes may be effected with respect to the details of construction and use of the invention without departing from the spirit and scope thereof as defined in the appended claims.

I claim:

1. A method for effecting surgery and therapy on humans and animals with lasers without undesired exposure of said humans, animals and other articles to stray laser beams, comprising the steps of
    (a) inserting a tubular article comprising at least one layer comprising a xerogel comprising at least one hydrophilic water-insoluble polymer, into the body cavity, of said human or animal, wherein said surgery or treatment is to be effected;
    (b) applying said laser to the desired site; and
    (c) as necessary, adding to said xerogel layer water or an aqueous solution of additive, if any, to replace water lost from said layer during said surgery or treatment; wherein said tubular element may, as desired, be hydrated before or after insertion.

2. The method of claim 1 wherein at least one layer on the side of the first layer opposite the side thereof first impacted by the stray laser beams is a metallic layer.

3. The method of claim 2 wherein said article comprises at least three layers wherein at least one layer on the side of said metal layer opposite the side facing the first xerogel layer comprises a hydrophilic xerogel.

4. The method of claim 3 wherein the surface of the metallic layer on the side of the first xerogel layer has been made nonreflective to laser beams.

5. The method of claim 2 wherein at least one one xerogel layer further comprising at least one pigment is interposed between said first xerogel layer and said metallic layer.

6. The method of claim 5 wherein the surface of the metallic layer on the side of the first xerogel layer has been made nonreflective to laser beams.

7. The method of claim 2 wherein the surface of said metal layer adjacent said first xerogel layer is nonreflective of laser beams.

8. The method of claim 7 further comprising a second hydrophilic xerogel layer interposed between said first xerogel and metallic layers wherein said second xerogel layer further comprises pigments selected from the group consisting of inorganic and organic pigments.

9. The method of claim 8 wherein said pigment is an inorganic pigment selected from the group consisting of $TiO_2$, ZnO, the basic white carbonates, sulfates, and silicates of lead, ZnO, lithopone, $Sb_2O_3$, $CaCO_3$, silicates of Mg and Al, pyrophillite, bentonite, mica, pumice, $BaSO_4$, $CaSO_4$, MgO, $SiO_2$, diatomite, and powders of Al, Cu, Zn, Pb, Au, Ag, Ni and their alloys, bronzes and Stainless Steel.

10. The method of claim 9 said pigment is $TiO_2$.

11. The method of claim 2 wherein said metal is selected from the group consisting of aluminum, titanium, silver, gold and their alloys.

12. The method of claim 11 wherein said metal is aluminum.

13. The method of claim 1 wherein said xerogel layer further comprises at least one pigment.

14. The method of claim 13 wherein the surface of the metallic layer on the side of the first xerogel layer has been made nonreflective to laser beams.

15. The method of claim 1 wherein said tubular element comprises at least two layers wherein the first layer, which is the first layer to be struck by the stray laser beams, comprises said xerogel.

16. The method of claim 15 wherein said first layer further comprises at least one pigment.

17. The method of claim 16 wherein the surface of the metallic layer on the side of the first xerogel layer has been made nonreflective to laser beams.

18. The method of claim 1 wherein at least one of said xerogel layers comprises at least one additive selected from the group consisting of pharmaceutically acceptable salts, colorants and, pigment medications.

19. The method of claim 1 wherein the hydrophilic water-insoluble polymer is selected from the group consisting of poly(ethylene oxide)s and copolymers of acrylonitrile with acrylamide.

20. The method of claim 19 wherein said polymer is a poly(ethylene oxide).

21. The method of claim 19 wherein said polymer is a poly(acrylonitrile-co-acrylamide).

* * * * *

UNITED STATES PATENT AND TRADEMARK OFFICE
CERTIFICATE OF CORRECTION

PATENT NO. : 4,977,904

DATED : Dec 18, 1990

INVENTOR(S) : Jack W. Kaufman

It is certified that error appears in the above-identified patent and that said Letters Patent is hereby corrected as shown below:

Sheet 4 of the drawing consisting of Figures 13-15 should be added as shown on the attached sheet.

Signed and Sealed this

Eighth Day of October, 1991

*Attest:*

HARRY F. MANBECK, JR.

*Attesting Officer*  *Commissioner of Patents and Trademarks*

FIG. 13
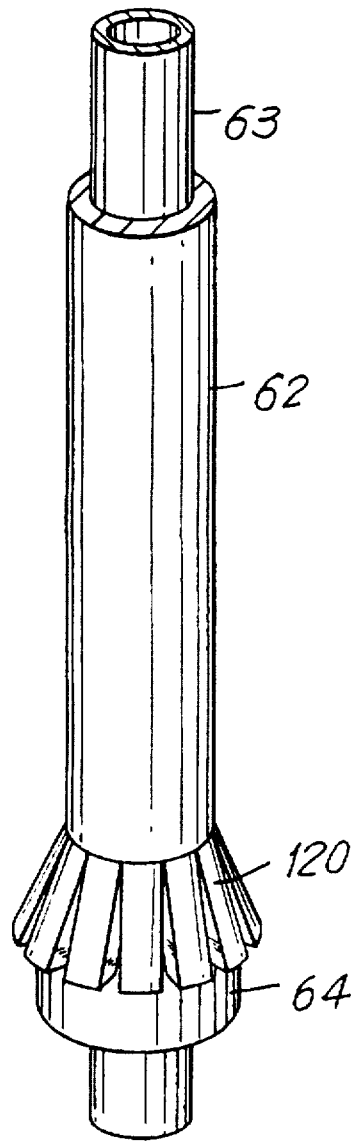
FIG. 14
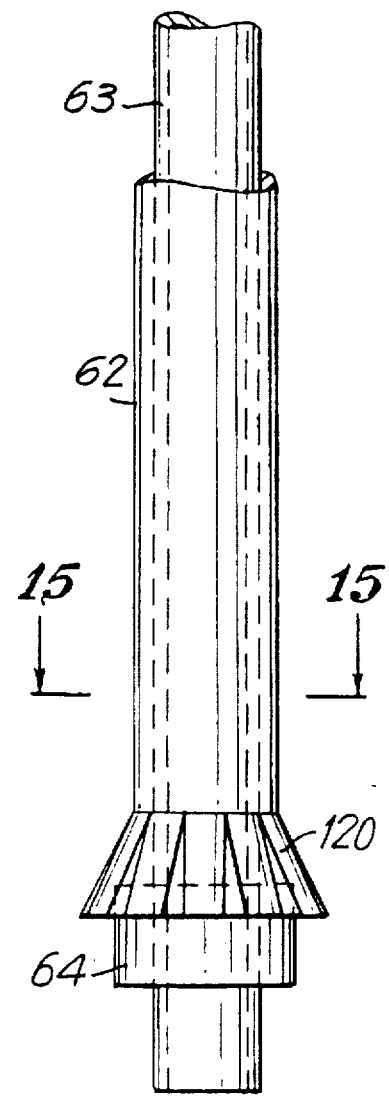
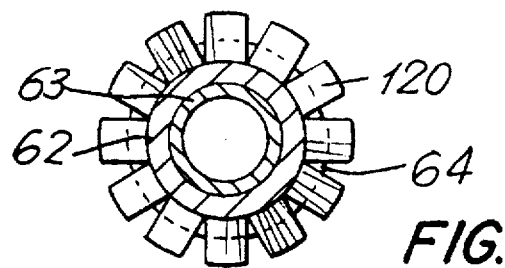
FIG. 15